US010448921B2

(12) United States Patent
Strassner et al.

(10) Patent No.: US 10,448,921 B2
(45) Date of Patent: *Oct. 22, 2019

(54) ULTRASOUND SYSTEMS AND METHODS FOR AUTOMATED FETAL HEARTBEAT IDENTIFICATION

(71) Applicant: KONINKLIJKE PHILIPS N.V., Eindhoven OT (NL)

(72) Inventors: Dorothy Anita Strassner, Eindhoven (NL); Ji Cao, Eindhoven (NL); Vijay Thakur Shamdasani, Eindhoven (NL); Intekhab Alam Mufti Mohammed, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 5 days.

This patent is subject to a terminal disclaimer.

(21) Appl. No.: 15/991,188

(22) Filed: May 29, 2018

(65) Prior Publication Data

US 2018/0271476 A1 Sep. 27, 2018

Related U.S. Application Data

(63) Continuation of application No. 15/027,050, filed as application No. PCT/IB2014/064575 on Sep. 17, 2014, now Pat. No. 9,993,224.

(Continued)

(51) Int. Cl.
*A61B 8/02* (2006.01)
*A61B 8/08* (2006.01)
(Continued)

(52) U.S. Cl.
CPC ............... *A61B 8/02* (2013.01); *A61B 5/14* (2013.01); *A61B 8/0866* (2013.01);
(Continued)

(58) Field of Classification Search
CPC ........ A61B 8/02; A61B 8/5269; A61B 8/5207; A61B 8/461; A61B 8/4483; A61B 5/14; A61B 8/486; A61B 8/469; A61B 8/0866
(Continued)

(56) References Cited

U.S. PATENT DOCUMENTS 5,515,856 A 5/1996 Olstad et al.
5,997,479 A 12/1999 Savord
(Continued)

FOREIGN PATENT DOCUMENTS

JP 2010193945 A 9/2010

OTHER PUBLICATIONS

M.E. Godfrey et al: "Fetal Cardiac Function: M-Mode and 4D Spatiotemporal Image Correlation", Fetal Diagnosis and Therapy, vol. 32, No. 1-2, Jan. 1, 2012 (Jan. 1, 2012), pp. 17-21.
(Continued)

*Primary Examiner* — Sanjay Cattungal

(57) ABSTRACT

Ultrasound systems and methods provide a workflow to automatically identify a fetal heartbeat. A region of interest (ROI) is identified in an ultrasound image and an ROI icon is positioned around or over a fetal pole and/or fetal heart. The ultrasound system produces spatially different M-mode lines associated with the ROI icon. The ultrasound system can identify a fetal heartbeat and estimate the fetal heart rate from echo signals received from echo signals associated with at least one of the spatially different M-mode lines. The echo signals for the M-mode lines can also be ranked according to the likely presence of a fetal heartbeat in the echo data.

14 Claims, 5 Drawing Sheets

Related U.S. Application Data

(60) Provisional application No. 61/886,694, filed on Oct. 4, 2013.

(51) Int. Cl.
*A61B 8/00* (2006.01)
*A61B 5/145* (2006.01)

(52) U.S. Cl.
CPC ............ *A61B 8/4483* (2013.01); *A61B 8/461* (2013.01); *A61B 8/469* (2013.01); *A61B 8/486* (2013.01); *A61B 8/5207* (2013.01); *A61B 8/5269* (2013.01)

(58) Field of Classification Search
USPC .................................................. 600/437–469
See application file for complete search history.

(56) References Cited

U.S. PATENT DOCUMENTS

| | | | |
|---|---|---|---|
| 6,436,048 B1 | 8/2002 | Pesque | |
| 6,582,367 B1* | 6/2003 | Robinson | A61B 8/14 600/443 |
| 9,149,249 B2* | 10/2015 | Matsunaga | A61B 8/02 |
| 9,179,892 B2* | 11/2015 | Haugen | A61B 8/0883 |
| 9,437,043 B2* | 9/2016 | Schauf | A61B 8/4488 |
| 2008/0125652 A1* | 5/2008 | Clark | A61B 8/02 600/437 |
| 2008/0221450 A1 | 9/2008 | Kim | |
| 2008/0281203 A1* | 11/2008 | Zhou | A61B 5/1075 600/450 |
| 2010/0185088 A1 | 7/2010 | Perrey | |
| 2010/0286521 A1* | 11/2010 | Betts | A61B 8/08 600/441 |
| 2012/0157834 A1* | 6/2012 | Lazebnik | A61B 8/0841 600/437 |
| 2013/0085392 A1 | 4/2013 | Shin | |
| 2013/0085393 A1 | 4/2013 | Schauf et al. | |
| 2016/0199029 A1* | 7/2016 | Struijk | A61B 8/0866 600/438 |
| 2017/0228525 A1* | 8/2017 | Wajs | G06F 21/36 |

OTHER PUBLICATIONS

J. Jürgens et al: "Three-dimensional multiplanar time-motion ultrasound or anatomical M-mode of the fetal heart: a new technique in fetal echocardiography", Ultrasound in Obstetrics and Gynecology, vol. 21, No. 2, Feb. 1, 2003 (Feb. 1, 2003), pp. 119-123.

* cited by examiner

64', 1', 128', 50'-76', 1, 2, 3, 64', 1', 128', 50-'76', 4, 5, 6, 64', 1', 128', 50-'76' ...

60', 63', 66', 69', 57'-72', 1, 2, 3, 60', 63', 66', 69', 57'-72', 4, 5, 6, ...

ULTRASOUND SYSTEMS AND METHODS FOR AUTOMATED FETAL HEARTBEAT IDENTIFICATION

CROSS-REFERENCE TO PRIOR APPLICATIONS

This application claims the benefit or priority of and describes relationships between the following applications: this application is a continuation of U.S. patent application Ser. No. 15/027,050, filed Apr. 4, 2016, which is the National Stage of International Application No. PCT/IB2014/064575, filed Sep. 17, 2014 which claims the priority of U.S. Provisional application 61/886,694 filed Oct. 4, 2013, all of which are incorporated herein in whole by reference.

Ultrasound is well suited for fetal imaging because it performs noninvasive imaging without exposing either the mother or the fetus to ionizing radiation. An objective of many fetal examinations is to assess the development of the fetal anatomy to determine whether the fetus is developing normally. As ultrasound image quality has improved over the years, more areas of the anatomy can be visualized for developmental assessment and in greater detail. Consequently, fetal ultrasound exams have become more thorough with increased requirements for anatomy that is to be assessed. One area of the anatomy that is greatly scrutinized is the developing fetal heart.

Ultrasound systems can be used to detect a fetal heartbeat within about five weeks of gestation. At this point, a normal fetal heart rate is similar to the mother's, e.g., about 80-85 beats per minute. The heart rate will steadily increase at about three beats per minute per day over the next month. After further development, a healthy fetal heart rate can range between 120 to 200 beats per minute (BPM). Accordingly, an ultrasound examination can be used to determine whether there is risk of a miscarriage if the fetal heartbeat not within an acceptable range of values. For example, a relationship between the fetal heart rate and risk of miscarriage at 6-8 weeks of pregnancy indicates about a one hundred percent chance of miscarriage if the fetal heart rate is less than seventy beats per minute. The chances of miscarriage decrease in line with an increasing measured heart rate, e.g., if the heart rate is less than ninety beats per minute the chances of miscarriage are still high at about an eighty-six percent chance of miscarriage.

In recent years the outflow tracts of the heart have become a focus of attention for detecting and measuring fetal heart rates. The cardiac outflow tracts of the fetal heart, however, can be difficult to image and detect for a useful period of measurement time. One reason for this is the small size of this fetal anatomy. Another reason is that it is desirable to not simply view the anatomy, but also the dynamics of the flow characteristics through the outflow tracts over the full fetal heart cycle. A further reason is that the outflow tracts undergo considerable development as the fetus grows, and consequently can have varying appearances and complexity depending on fetal age. The outflow tracts can thus be difficult to identify on the ultrasound display, and it can be even more difficult to acquire images in the proper orientation for adequate detection and/or measurement of a fetal heartbeat.

Another problem is that the fetus frequently moves and may not remain stationary during the time needed for data acquisition. When the fetus moves, the orientation of the desired image data relative to the probe will change, and the fetal heart may leave the field of view entirely, resulting in an absence of the desired anatomy from the acquired data set. Also, fetal movement during the acquisition can limit the accuracy of the measurement of the fetal heart cycle. In addition, it can also be difficult to distinguish the fetal heart rate from the mother's heart rate and/or other rhythmic background artifacts.

Thus, there is a need for improved systems and workflows for the clinician that makes ultrasound systems easier to use and more accurate for identifying a fetal heartbeat and measuring a fetal heart rate.

The present invention relates to medical diagnostic systems and, in particular, to ultrasonic diagnostic imaging systems for identifying a fetal heartbeat and an associated heart rate.

In accordance with the principles of the present invention, a diagnostic ultrasound system has a workflow and controls that facilitate identifying a heartbeat (e.g., a fetal heartbeat) and an associated heart rate. The workflow enables the clinician to set a region of interest (ROI) about the fetal pole and/or fetal heart and then identify a fetal heart beat and/or acquire a fetal heart rate. The ultrasound system is automated to repetitively scan differently oriented M-mode lines associated with the region of interest. The ultrasound system can identify a fetal heartbeat and estimate the fetal heart rate from echo signals received along at least one of the M-mode lines. The echo signals from the M-mode lines can also be ranked, for example, to identify the M-mode scan most likely to be indicative of a heartbeat in the echo data.

The present invention provides systems and methods for identifying a heartbeat (e.g., a fetal heartbeat) and an associated heart rate. The systems and methods can be used, for example, to reduce scanning times for sonographers, increase diagnostic confidence and simplify workflows for scanning maternal patients.

In one embodiment, the present invention includes an ultrasonic imaging system for identifying a fetal pole or heart and/or the associated heart rate. The systems of the present invention include an ultrasound probe. A variety of probes can be used and can include an array transducer. The systems also include an image processor that processes echo data from the probe. The echo data can include echo signals obtained by a variety of imaging modes such as B-mode or M-mode image acquisition. The systems also can transmit the echo data and/or display the echo data from the probe for viewing. Image displays in the system are coupled to the image processor and adapted to display an ultrasound image including a fetal heart. A graphics generator in the system responds to a user control that identifies an ROI in the ultrasound image. For example, the ROI can be identified in the vicinity of a fetal pole or fetal heart in the ultrasound image using an ROI icon. A user control in the system is further adapted to initiate generation of spatially different M-mode lines associated with the region of interest. In one example, an ROI can be identified in the ultrasound image by user manipulation of a graphic icon and spatially different M-mode lines (e.g., between two to fifty M-mode line locations) can be displayed in relation to the ROI. The system acquires echo data (e.g., M-mode and/or B-mode echo signals) repetitively from some or all of the spatially different M-mode lines. The echo data is analyzed by the system or transmitted for analysis to identify whether a fetal heartbeat is discernible in the M-mode image acquired from at least one of the M-mode line positions. Some, one or none of the temporally acquired echo data corresponding to each of the spatially different M-mode lines may exhibit echo signals indicative of the fetal heartbeat. Furthermore, the acquired echo data can be ranked based on fetal heart rates measured in the echo data of the M-mode lines that registered a fetal heartbeat. In some embodiments, a maternal heartbeat and/or heart rate can be identified in place of or in addition to the fetal heartbeat.

Figure 1:
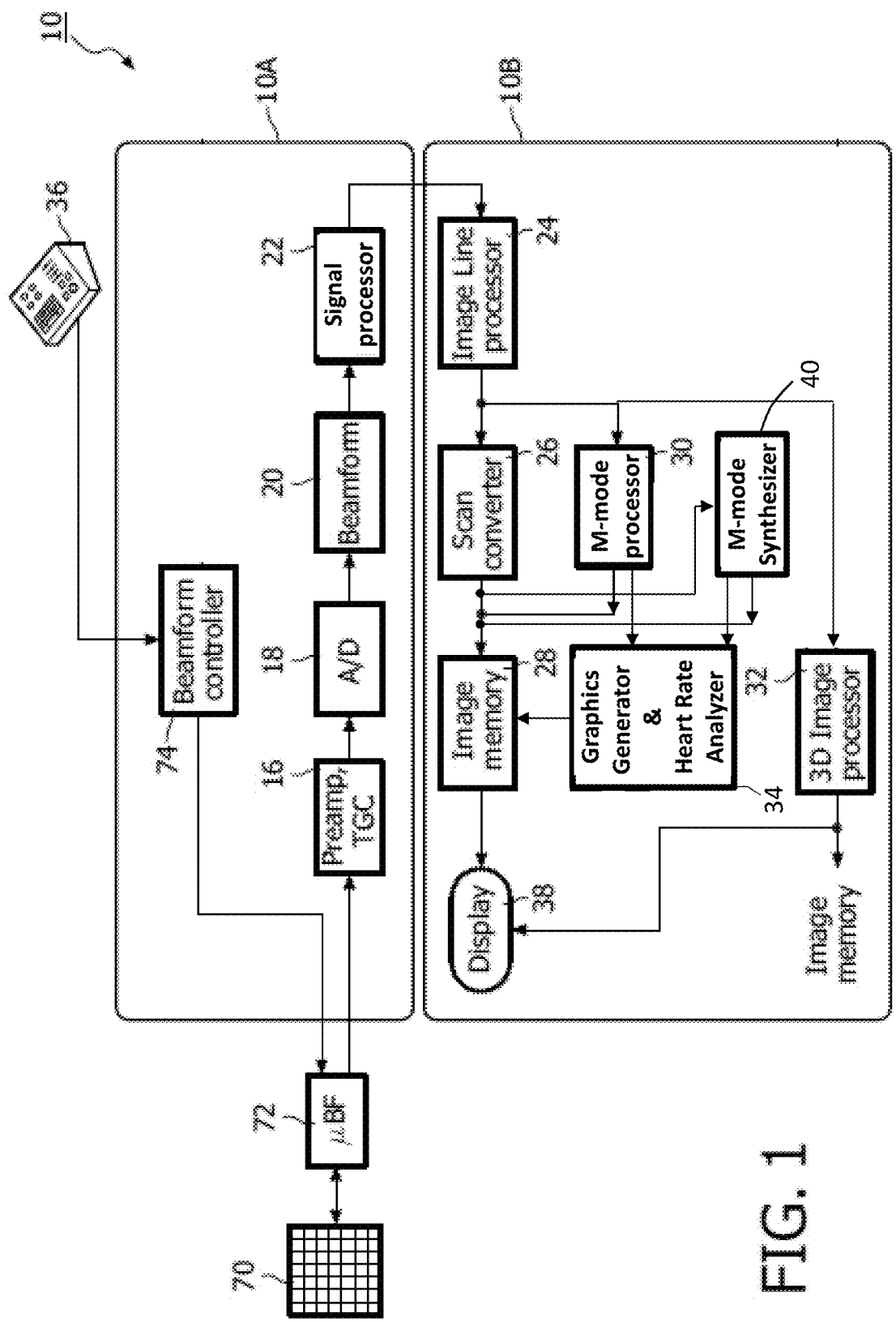
FIG. 1 illustrates in block diagram form an ultrasonic diagnostic imaging system constructed in accordance with the principles of the present invention.

Referring to FIG. 1, an ultrasound system 10 constructed in accordance with the principles of the present invention is shown in block diagram form. The ultrasound system is configured by two subsystems, a front end acquisition subsystem 10A and a display subsystem 10B. An ultrasound probe is coupled to the acquisition subsystem which includes a two-dimensional matrix array transducer 70 and a micro-beamformer 72. Linear or curved array transducers can also be used. In some embodiments, only one plane of the matrix array will be used for M-mode or B-mode image acquisition. The micro-beamformer contains circuitry which control the signals applied to groups of elements ("patches") of the array transducer 70 and does some processing of the echo signals received by elements of each group. Microbeamforming in the probe advantageously reduces the number of conductors in the cable between the probe and the ultrasound system and is described, e.g., in U.S. Pat. No. 5,997,479 (Savord et al.) and in U.S. Pat. No. 6,436,048 (Pesque), each of which is incorporated by reference herein.

The probe is coupled to the acquisition subsystem 10A of the ultrasound system. The acquisition subsystem includes a beamform controller 74 which is responsive to a user control 36 and provides control signals to the microbeamformer 72, instructing the probe as to the timing, frequency, direction and focusing of transmit beams. The beamform controller 74 controls the beamforming of echo signals received by the acquisition subsystem by its control of analog-to-digital (A/D) converters 18 and a beamformer 20. Echo signals received by the probe are amplified by preamplifier and TGC (time gain control) circuitry 16 in the acquisition subsystem, and then digitized by the A/D converters 18. The digitized echo signals can then be formed into fully steered and focused beams by the beamformer 20. The echo signals are processed by a signal processor 22, which performs digital filtering and can also perform other signal processing such as harmonic separation, speckle reduction, and other desired image signal processing.

The echo signals produced by the acquisition subsystem 10A are coupled to the display subsystem 10B, which processes the echo signals for display in the desired image format. The echo signals are processed by an image line processor 24, which is capable of sampling the echo signals or assembling echoes of a given beam into complete line signals. For M-mode image acquisition, at least one of the line signals output from the image line processor 24 can be directed to an M-mode processor 30. The M-mode processor generates M-mode images that are stored in the image memory 28 and displayed on display 38. For B-mode image acquisition, the image lines for a 2D image are scan converted into the desired image format by a scan converter 26 which performs R-theta conversion as is known in the art. The 2D image is stored in the image memory 28 and displayed on the display 38.

In some embodiments, the 2D image data from the scan converter is output to an M-mode synthesizer 40, which can generate M-mode images from the 2D image data. As discussed further below, echo signals from the B-mode lines can be synthesized to generate echo data associated with an M-mode line of interest. The synthesized M-mode images from B-mode echo signals are further output to the image memory 28 and displayed. The image in memory can also be overlaid with graphics to be displayed with the image, which are generated by a graphics generator 34 which is responsive to the user control 36. The graphics generator 34 also communicates with the M-mode processor 30 and/or the M-mode synthesizer 40 to correlate the image location of an associated M-line with the normal and/or synthesized M-mode echo data for the corresponding M-line. A heart rate synthesizer 34 also communicates with the M-mode processor 30 and/or the M-mode synthesizer 40 to apply algorithms, such as image analysis and/or frequency analysis algorithms, to the normal and/or synthesized M-mode echo data to calculate a fetal heart rate. The heart rate analyzer 34 can also rank the M-mode echo data according to the likely presence of a heartbeat in the echo data.

The normal and/or synthesized M-mode echo data can be stored in the image memory 28 for future access or it can be displayed in real-time. Stored echo data can be stored by way of previously acquired cine loops of B-mode images that can later be processed to calculate a heart rate using synthesized M-mode echo data. During real-time imaging, motion compensation may be applied to track the overall motion of the fetus. Motion compensation is described, for example, in U.S. Pat. No. 6,589,176, which is herein incorporated by reference.

The system can be designed for 1D, 2D, and/or 3D ultrasound imaging. In certain embodiments, 2D imaging can be used to achieve high frame rates for image acquisition. Frame rates on the order of tens to hundreds of frames per second can be used to record echo signals from a fetal heartbeat. If real-time volumetric imaging is used, the display subsystem 10B includes a 3D image rendering processor 32 which receives image lines from the image line processor 24 for the rendering of real-time three dimensional images. The 3D images can be displayed as live (real time) 3D images on the display 38 or coupled to the image memory 28 for storage of the 3D data sets for later review and diagnosis.

Figure 2:
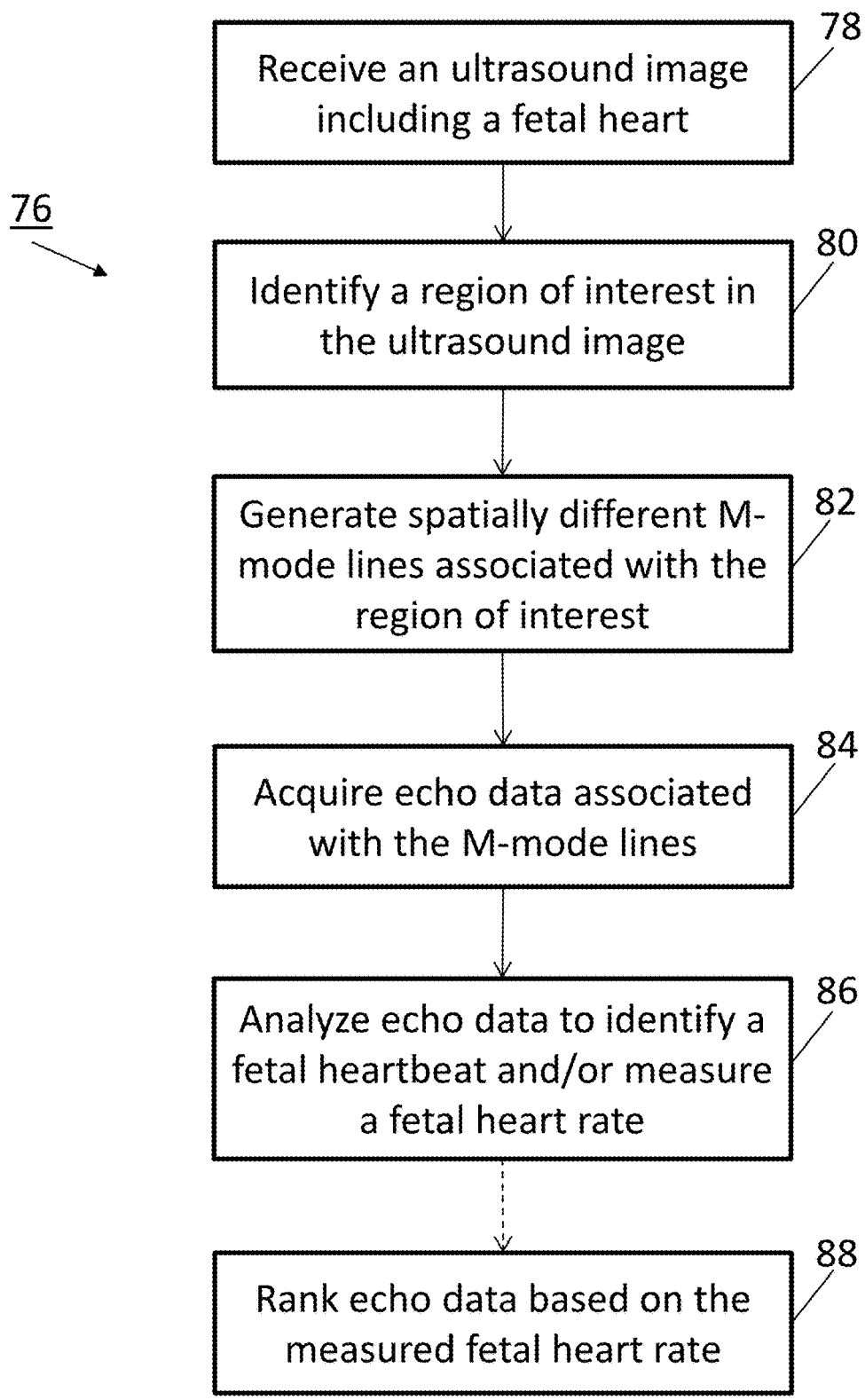
FIG. 2 illustrates a workflow in accordance with the present invention for identifying and measuring a fetal heart rate.

FIG. 2 is a flow chart showing the workflow 76 of an implementation of the present invention. This workflow 76 begins with a step 78 of receiving an image of a fetal heart. In one embodiment, the image or images of the fetal heart can be acquired during a scanning procedure and, while scanning the fetus, the sonographer can identify an ROI as described herein.

In another embodiment, a sonographer can acquire a plurality of ultrasound images including the fetal pole and/or fetal heart that can be stored (e.g., in a cine loop) and reviewed after scanning. After the scan, the sonographer can identify the ROI based on the collected images.

In step 80, an ROI in the ultrasound image is identified. In some embodiments, the location in the anatomy from which temporally discrete echo signals are acquired can be set to a default image location such as the center of an image displayed during scanning or in images in an acquired loop of images. Alternatively, a location in displayed or acquired images can be designated by the user by manipulation of a control of the user controls in the system as discussed below in conjunction with FIG. 4. For instance, the user can manipulate a joystick, trackball, or other control of the user controls to locate an ROI designation icon over a region of interest in an image containing a fetal heart. In certain embodiments, the ROI in the image is identified on the display screen by an ROI icon as discussed below, which can be positioned completely or partially around or over the fetal pole and/or fetal heart. A variety of ROI icons can be used. For example, the ROI icon may be square, circular, oval or rectangular shaped. The ROI icons may also be a simple point, an X, or a crosshair indicator. In some embodiments, the ROI can be identified by positioning a mouse cursor over the ROI of the image.

In step 82, a plurality of spatially different M-mode lines that are associated with the region of interest are generated. The M-mode lines can be generated and visualized on the display or they can be invisible with only the ROI icon being shown in the display. The M-mode lines are generated in relation to the ROI icon and are spatially distributed over the region of interest in a variety of ways. For example, if a circular ROI icon is used, the M-mode lines can be positioned as lines spanning a diameter of the circle. Alternatively, parallel line patterns or crosshatch patterns could be positioned within an ROI icon, such as a circle or a square. Generally, M-mode line patterns (e.g., random, radial, parallel, crosshatch, and/or honeycomb patterns) can be used for any shape or type of ROI icon. Preferably, the spatially distributed M-mode lines are automatically generated by a system of the present invention. Spatially different M-mode lines can also be generated as directed by a user by drawing lines in the relation to the ROI icon. The system can also select a specific number of spatially different M-mode lines to be used. In some embodiments, the number of spatially different M-mode lines ranges between 2 to 100, between 5 to 50, between 10 to 50, or between 10 to 40.

The workflow also includes step 84, which is acquiring echo data associated with the spatially different M-mode lines. In some embodiments, the echo data can be repetitively acquired during a scanning procedure by M-mode image acquisition from a plurality of the spatially different M-mode lines associated with the ROI. Alternatively, the echo data can include echo signals from B-mode image acquisition. Here, the M-mode synthesizer synthesizes the echo data for a selected M-mode line by combining echo signals from B-mode image lines that intersect a given M-mode line position. Synthesizing the echo data associated with a selected M-mode line can be conducted in real-time during scanning as described below with regards to FIG. 5. A similar process can be used to synthesize echo data from a plurality of B-mode images that are stored and later analyzed.

In step 86, the echo data of an M-line image is analyzed to identify a fetal heartbeat and/or measure the associated fetal heart rate. As described below, the techniques for doing this include detecting motion of the fetal heart through analysis of the temporal echo data for an M line positioned through the fetal heart. As shown in step 88, the workflow can optionally include a ranking step that preferentially ranks the recorded echo data for identification of a fetal heart rate from some or all of the spatially different M-mode lines.

A method of the present invention is carried out using ultrasound systems as described herein. The ultrasound systems can operate to perform any of the following steps: receive an ultrasound image including a fetal pole or heart, identify a region of interest (ROI) in the ultrasound image, generate a plurality of spatially different M-mode lines associated with the region of interest, acquire echo data corresponding to the spatially different M-mode lines, and analyze the echo data to identify a fetal heartbeat associated with at least one of the spatially different M-mode lines.

Figure 3:
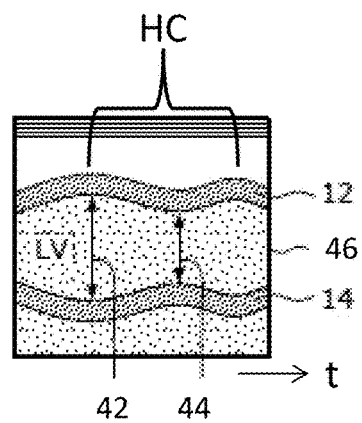
FIG. 3 illustrates an M-mode image of the motion of the heart muscle.

As described herein, M-mode lines are generated and used to detect motion of the fetal heart so as to identify a fetal heart and/or measure a fetal heart rate. FIG. 3 illustrates a technique for detecting motion using M mode imaging with an M line positioned through the fetal heart. In particular, FIG. 3 shows an M mode image 46 produced by an M line positioned such that it extends through the left ventricle (LV) of the fetal heart. When positioned in this manner, the M line will pass through the myocardial wall 12 on one side of the fetal heart, through the chamber of the LV, and through the myocardial tissue 14 on the other side of the heart. An ultrasound beam is transmitted along this M line direction through the LV periodically, and the received A-line from each transmission is shown on the display in a scrolling manner alongside the previously received A-lines. The result is an M mode image as shown in FIG. 3 where the opposite sides of the heart chamber are most greatly separated when the fetal heart is relaxed at the end diastole point in the heart cycle as indicated by arrow 42. The opposite walls of the heart chamber are in closest proximity at the peak systole phase of the heart cycle as indicated by arrow 44. FIG. 3 illustrates this cyclical pattern of the movement of the heart wall as the fetal heart contracts and expands with each heartbeat. By tracking the changing position (motion) of the heart wall 12 or 14, a waveform in phase with the heart cycle HC can be produced. The waveform is further measured to determine the heart rate, e.g., by measuring from peak-to-peak (or valley to valley) periodicity of successive waves.

Figure 4:
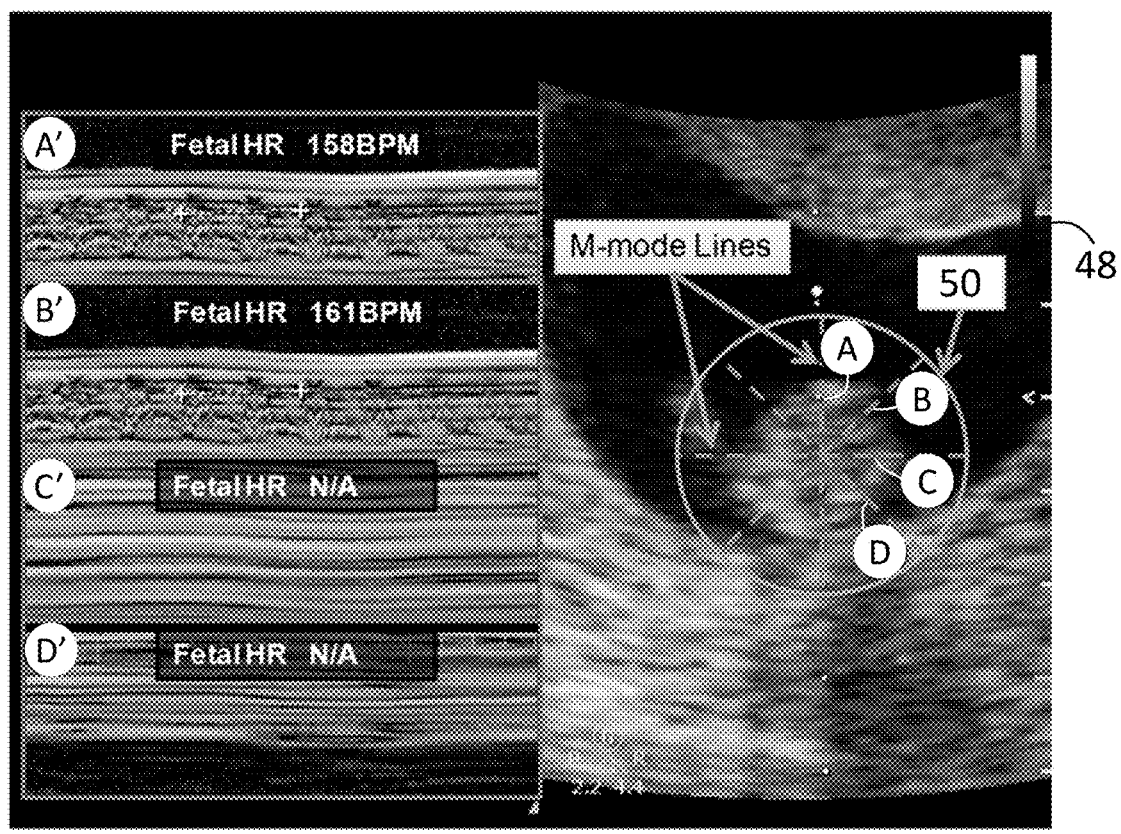
FIG. 4 illustrates a display of an implementation of the present invention for identifying an ROI in the image including the fetal heart and overlaying spatially different M-mode lines for identifying and measuring a fetal heart rate.

FIG. 4 illustrates an ultrasound display generated in accordance with one embodiment of the present invention. As shown, an ROI is identified in ultrasound image 48 by ROI icon 50, which has been positioned over a fetal heart as shown in ultrasound image 48. Spatially different M-mode lines identified as M-mode lines A, B, C and D are arranged in the ROI icon 50. In this example, the M-mode lines are arranged radially to span diameters of the circular ROI icon, which is positioned over the fetal heart. As described further herein, the echo data corresponding to M-mode lines A, B, C and D is acquired and analyzed to identify a fetal heart beat and to measure the fetal heart rate. Here, for example, panel A' shows that the echo data for M-mode line A registered a fetal heart rate of 158 beats per minute and panel B' shows that the echo data for M-mode line B registered a fetal heart rate of 161 beats per minute. Panels C' and D' show that the M-mode lines C and D did not register a fetal heart rate. The images in the panels A' and B' include a representation of movement of the fetal heart as registered from M-mode image acquisition.

For measuring heart rate, the M-mode displays in panels A' and B' are analyzed for pulsatile motion. A waveform in an M-mode scan represents the movement of the beating fetal heart as described in FIG. 3. As shown in panels A' and B', a white measuring line can be used to measure time between individual heart cycles. In one example, by pressing a freeze button in the system, a user can use a caliper function to measure the fetal heart cycle, in which the graphics generator 36 displays the white measuring line to measure time between individual heartbeats. This can be done by measuring from peak-to-peak (or valley to valley) of two subsequent waves. Using the heart rate analyzer 34, a software calculation can turn a measurement of the duration of a heart cycle HC into a calculated fetal heart rate by processing data from the M-mode processor 30 and/or M-mode synthesizer 40 or by accessing data from the image memory 28.

Figure 5:
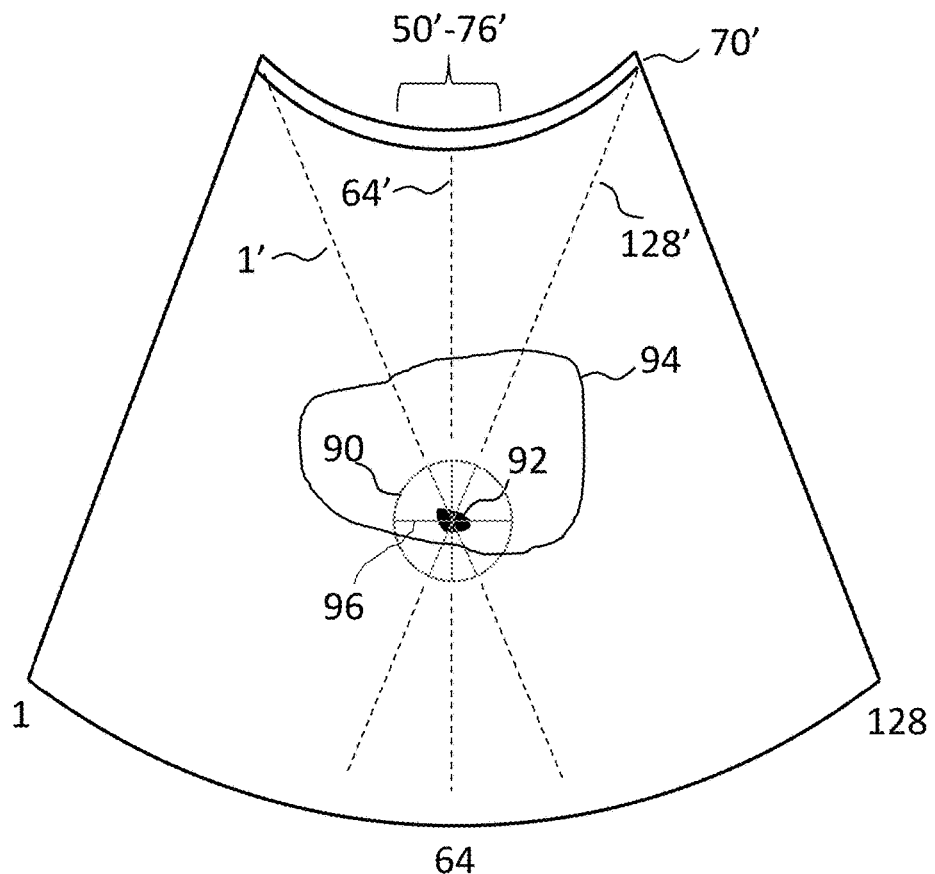
FIG. 5 illustrates a technique for automatically identifying a fetal heart beat and measuring a fetal heart rate.

In an implementation of the present invention, a sonographer views the fetal heart and the mother's uterus in real-time using B-mode imaging. The B-mode images can, in some embodiments, be stored in a cine loop for later analysis to determine the fetal heart rate. Concurrently or separately, the sonographer can generate the echo data necessary to measure the fetal heart beat using M-mode and/or B-mode image acquisitions. FIG. 5 illustrates an embodiment using a curved linear array transducer 70' having 128 scan lines to image and analyze the fetal heart 92 in a mother's uterus 94 (fetus not shown). The area scanned by the transducer for a B-mode image spans from scanline 1 to scanline 128, with scanline 64 in the middle. Preferably, repetitive B-mode image acquisition over the 128 scan lines generates real-time images for the sonographer to use for positioning an ROI icon 90 around the fetal heart 92. M-mode lines that span the circular ROI icon correspond to beams from the array transducer that can be generated with or without beam steering. As shown, beam line 1', 64' and 128' are used to generate M-mode images corresponding to three of the M-mode lines associated with the ROI icon. The horizontal M-mode line 96 is synthesized using B-mode echo signals that are produced during B-image acquisition. As represented by the bracket in FIG. 5, beams from scan lines 50' through 76' of the array transducer are used to generate echo signals from positions along the horizontal M-line 96 to produce a synthesized M-mode image.

M-mode image acquisition and B-mode image acquisition can be performed in various sequences to produce both M-mode images (normal or synthesized) as well as B-mode images for real-time imaging by the sonographer. As shown, M-mode image echo signals are acquired along beams 1', 64' and 128' to produce echo data associated with the corresponding M-mode lines on the display. The echo signals used to synthesize the horizontal M-line are collected next by scanning beams 50'-76'. Echo signals from beams 1-3 are acquired and used in generated a B-mode image for display to the sonographer. This sequence of data acquisition can proceed until a 128 scanline B-mode image is produced, during which echo data is acquired from the M-line locations multiple times, at a much higher M-line scan rate than the B-mode frame rate. The process is then repeated. Alternative sequences can also be used. For example, the B-mode image could be acquired in the first portion of a scan, followed by full collection of echo data for beams 1', 64', and 128' and then the synthesized B-mode echo signals for beams 50'-76'.

Depending on the positioning of the M-mode lines in the ROI, at least one of the imaging lines may extend through the left ventricle (LV) of the fetal heart. When positioned in this manner, the imaging beam (64' in this example) will pass through the myocardial wall on one side of the fetal heart, through the chamber of the LV, and through the myocardial tissue on the other side of the heart. In M-mode image acquisition, the result is an M mode image as shown in panels A' and B' of FIG. 4 where the opposite sides of the heart chamber are most greatly separated where a cyclical pattern of the movement of the heart wall as the fetal heart contracts and expands with each heartbeat can be recorded.

Figure 6A:
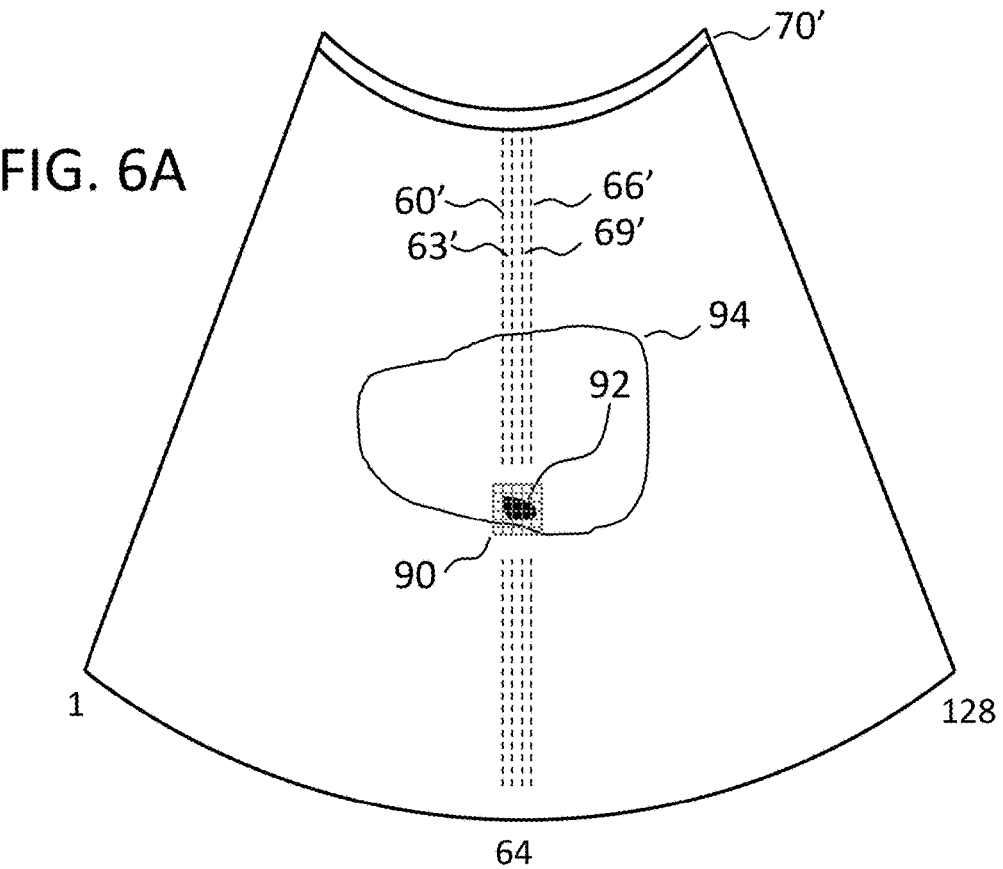
FIG. 6A illustrates another technique for automatically identifying a fetal heart beat and measuring a fetal heart rate.
Figure 6B:
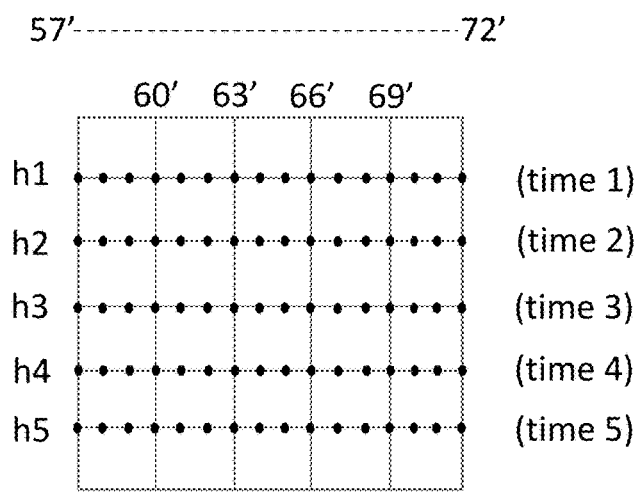
FIG. 6B illustrates a technique for measuring fetal heart beat signals by synthesizing M-line data from B-mode echo signals.

FIGS. 6A and 6B illustrate another embodiment of collecting echo data corresponding to M-mode lines associated with an ROI of an ultrasound image. A curved linear array transducer 70' is used to collect echo signals associated with M-mode lines associated with the ROI in the ultrasound image. As shown in FIG. 6A, a grid pattern is used for the ROI icon 90 that is positioned over the fetal heart 92 in the mother's uterus 94. The M-mode lines in the grid pattern correspond to M-mode imaging beams 60', 63', 66' and 69' that propagate in parallel through the ROI in the image. Echo data corresponding to the horizontal M-mode lines h1-h5 can be acquired using echo signals generated by beams 57'-72', which are not shown in FIG. 6A for clarity. As shown in FIG. 6B, echo signals at specific time points along beams 57'-72' are acquired and used to synthesize M-mode images for the horizontal M-mode lines h1-h5. As shown by the black dots in FIG. 6B, echo signals along beams 57'-72' are acquired at time 1, time 2, time 3, time 4, and time 5 along the beams used to generate the horizontal M-mode lines. Furthermore, the acquisition of the data can be collected using various sequences. Here, echo signals are acquired first along beams 60', 63', 66, and 69' for four normal M-mode displays. Echo signals are then collected from beams 57'-72' for synthesizing the M-mode images of the horizontal M-lines. Echo signals for B-mode image display to the sonographer can be collected along beams at intervals of three (e.g., for scan lines 1, 2, and 3, followed later by 4, 5, and 6, and so on). Alternative sequences can be used. For example, the B-mode image could be acquired in the first portion of a scan, followed by full collection of the M-mode images for beams 60', 63', 66, and 69' and then the synthesized B-mode echo signals for beams 57'-76'.

What is claimed is:

1. An ultrasonic diagnostic imaging system for identifying a fetal heartbeat, the system comprising:
   an ultrasound probe including an array transducer;
   an image processor adapted to process echo data from the probe for display;
   an image display coupled to the image processor and adapted to display an ultrasound image including a fetal heart; and
   a user control adapted to initiate generation of a plurality of spatially different M-mode lines associated with a region of interest in the ultrasound image,
   wherein the imaging system is adapted to:
   acquire echo data corresponding to the spatially different M-mode lines;
   analyze the echo data to measure fetal heart rates from the spatially different M-mode lines;
   rank the echo data of the spatially different M-mode lines based on the measured fetal heart rates; and
   identify, using the ranked echo data, the fetal heartbeat associated with at least one of the spatially different M-mode lines.

2. The system of claim 1, wherein the system is further adapted to measure a fetal heart rate from the echo data corresponding to the M-mode lines.

3. The system of claim 1, wherein at least some of the spatially different M-mode lines are automatically generated by the system.

4. The system of claim 1, wherein at least some of the spatially different M-mode lines are generated by the system as directed by a user.

5. The system of claim 1, wherein the system is adapted to acquire the echo data corresponding to at least some of the spatially different M-mode lines using M-mode or B-mode image acquisition.

6. The system of claim 1, wherein the system is adapted to synthesize echo data corresponding to at least some of the spatially different M-mode lines by combining echo signals from a plurality of B-mode image lines produced by the array transducer that intersect a given M-mode line.

7. A method of using ultrasound imaging to identify a fetal heartbeat, the method comprising:
 receiving an ultrasound image including a fetal heart;
 identifying a region of interest (ROI) in the ultrasound image;
 generating a plurality of spatially different M-mode lines associated with the region of interest;
 acquiring echo data corresponding to the spatially different M-mode lines;
 analyzing the echo data to measure fetal heart rates from the spatially different M-mode lines;
 ranking the echo data of the spatially different M-mode lines based on the measured fetal heart rates; and
 identifying, using the ranked echo data, a fetal heartbeat associated with at least one of the spatially different M-mode lines.

8. The method of claim 7, comprising determining a fetal heart rate based on the echo data corresponding to at least one of the spatially different M-mode lines.

9. The method of claim 7, wherein the spatially different M-mode lines are automatically generated by a computer system, generated by the computer system as directed by a user, or a combination thereof.

10. The method of claim 7, wherein acquiring the echo data comprises using M-mode or B-mode image acquisition.

11. The method of claim 7, wherein the receiving comprises receiving a plurality of B-mode ultrasound images stored in a cine loop, and the acquiring comprises synthesizing echo data from the B-mode images.

12. A computer system for identifying a fetal heartbeat, the computer system comprising instructions that when executed cause the system to:
 receive an ultrasound image including a fetal heart;
 identify a region of interest (ROI) in the ultrasound image;
 generate a plurality of spatially different M-mode lines associated with the region of interest;
 acquire echo data corresponding to the spatially different M-mode lines;
 analyze the echo data to measure fetal heart rates in the spatially different M-mode lines;
 rank the echo data of the spatially different M-mode lines based on the measured fetal heart rates; and
 identify, using the ranked echo data, a fetal heartbeat associated with at least one of the spatially different M-mode lines.

13. The computer system of claim 12, further comprising instructions that when executed cause the system to determine a fetal heart rate based on the echo data corresponding to at least one of the spatially different M-mode lines.

14. The computer system of claim 12, wherein the receive step comprises receiving a plurality of B-mode ultrasound images stored in a cine loop, and the acquiring comprises synthesizing echo data from the B-mode images.

* * * * *